(12) United States Patent
Akashi et al.

(10) Patent No.: US 10,116,871 B2
(45) Date of Patent: Oct. 30, 2018

(54) TUNNEL LINING SURFACE INSPECTION SYSTEM AND VEHICLE USED FOR TUNNEL LINING SURFACE INSPECTION SYSTEM

(71) Applicant: WEST NIPPON EXPRESSWAY ENGINEERING SHIKOKU COMPANY LIMITED, Takamatsu-shi, Kagawa (JP)

(72) Inventors: Yukio Akashi, Takamatsu (JP); Kazuaki Hashimoto, Takamatsu (JP); Shogo Hayashi, Takamatsu (JP)

(73) Assignee: WEST NIPPON EXPRESSWAY ENGINEERING SHIKOKU COMPANY LIMITED, Takamatsu-shi, Kagawa (JP)

( * ) Notice: Subject to any disclaimer, the term of this patent is extended or adjusted under 35 U.S.C. 154(b) by 173 days.

(21) Appl. No.: 14/903,623

(22) PCT Filed: Dec. 3, 2014

(86) PCT No.: PCT/JP2014/082021
§ 371 (c)(1),
(2) Date: Jan. 8, 2016

(87) PCT Pub. No.: WO2016/013132
PCT Pub. Date: Jan. 28, 2016

(65) Prior Publication Data
US 2016/0227126 A1    Aug. 4, 2016

(30) Foreign Application Priority Data
Jul. 25, 2014   (JP) .................................. 2014-152322

(51) Int. Cl.
*H04N 5/232*      (2006.01)
*G01N 21/954*     (2006.01)
(Continued)

(52) U.S. Cl.
CPC ....... *H04N 5/23296* (2013.01); *G01N 21/954* (2013.01); *G06T 7/0008* (2013.01);
(Continued)

(58) Field of Classification Search
CPC ................................. G01B 11/24; G01C 15/00
See application file for complete search history.

(56) References Cited

FOREIGN PATENT DOCUMENTS

| JP | 9-284749 A | 10/1997 |
|----|------------|---------|
| JP | 2003-185589 A | 7/2003 |

(Continued)

OTHER PUBLICATIONS

International Search Report for PCT/JP2014/082021 dated Jan. 20, 2015.

*Primary Examiner* — William C Vaughn, Jr.
*Assistant Examiner* — Jerry Jean Baptiste
(74) *Attorney, Agent, or Firm* — Sughrue Mion, PLLC

(57) ABSTRACT

The invention is aimed that the soundness (degree of deterioration) of a tunnel can be inspected according to each span. The image synthesis processing is performed to obtain the image showing both sides of the tunnel lining surface according to the each span of the tunnel lining surface, by comparing the first image photographied by the photography means, showing one side face in both side faces of the tunnel lining surface, while the photography means is fixed to the first photography position, and the second image photographied by the photography means, showing the other side face in both side faces of the tunnel lining surface, while the photography means is fixed to the second photography position, and indicating the portions forming the identical span of the tunnel lining surface.

3 Claims, 16 Drawing Sheets

(51) Int. Cl.
*G06T 7/00* (2017.01)
*H04N 5/225* (2006.01)
*H04N 5/369* (2011.01)

(52) U.S. Cl.
CPC ......... *H04N 5/2252* (2013.01); *H04N 5/2253* (2013.01); *H04N 5/2256* (2013.01); *H04N 5/2258* (2013.01); *H04N 5/23229* (2013.01); *G01N 2201/062* (2013.01); *G01N 2201/12* (2013.01); *G06T 2207/20221* (2013.01); *G06T 2207/30108* (2013.01); *G06T 2207/30184* (2013.01); *H04N 5/3692* (2013.01)

(56) References Cited

FOREIGN PATENT DOCUMENTS

| | | | | | |
|---|---|---|---|---|---|
| JP | 2012-220471 | A | | 11/2012 | |
| JP | 2012220471 | A | * | 11/2012 | ............. G01B 11/24 |
| JP | 2014-95627 | A | | 5/2014 | |
| JP | 2014095627 | A | * | 5/2014 | ............. G01B 11/00 |

* cited by examiner fig.12
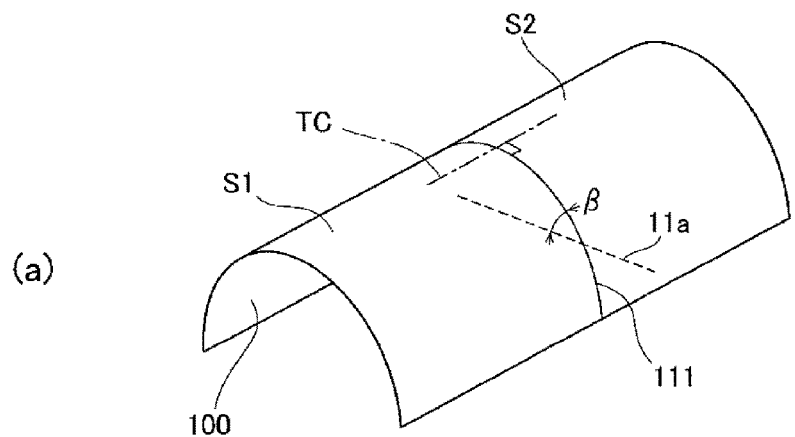
(a)
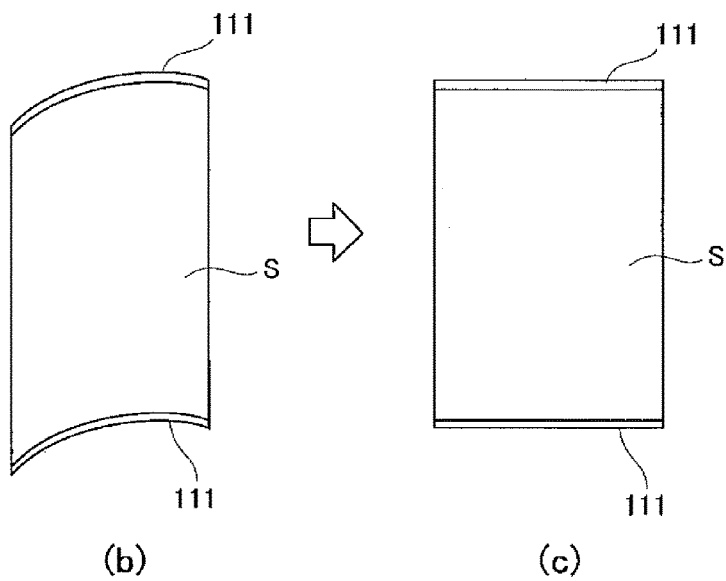
(b) (c)

TUNNEL LINING SURFACE INSPECTION SYSTEM AND VEHICLE USED FOR TUNNEL LINING SURFACE INSPECTION SYSTEM

CROSS REFERENCE TO RELATED APPLICATIONS

This application is a National Stage of International Application No. PCT/JP2014/082021filed Dec. 3, 2014, claiming priority based on Japanese Patent Application No. 2014-152322 filed Jul. 25, 2014, the contents of all of which are incorporated herein by reference in their entirety.

TECHNICAL FIELD

The present invention relates to the tunnel lining surface inspection system and the vehicle used for the tunnel lining surface inspection system, in particular to the system and the vehicle for inspecting soundness (degree of deterioration) of a tunnel by image-visualizing faulted conditions such as cracking on the tunnel lining surface.

BACKGROUND ARTS

The applicant has already proposed the tunnel lining surface inspection system in which, while a vehicle is travelling in the tunnel, the tunnel lining surface image is photographed by the photography means mounted in the vehicle and is processed into the image used for inspecting the tunnel lining surface, as shown in the Patent document 1.

According to the invention proposed in the Patent document 1, the tunnel lining surface image can be obtained while a vehicle travels, and, by using the image, the soundness (degree of deterioration) of a tunnel can be inspected by image-visualizing the faulted conditions such as cracking on the tunnel lining surface.

the Patent document 1: Japanese Patent Application Laid-open No. 2014-95627

DISCLOSURE OF INVENTION

Problems to be Solved by the Invention

The tunnel lining surface is constituted according to one span. The joint divides the tunnel lining surface according to one span, and each span is given a span number (lining number) for identifying the portion of the tunnel lining surface.

Accordingly, when the soundness (degree of deterioration) of a tunnel is inspected, it is desired that measures are planned by managing the images according to the each span number (lining number) and extracting the situations in which such abnormal situations as width, length, direction, shape, density of cracking, presence of water leakage and efflorescence are occurring.

The present invention has been made by taking such actual situations into account, and aims at being able to inspect the soundness (degree of deterioration) of a tunnel according to each span by processing the tunnel lining surface images obtained while a vehicle travels into the images indicating both side faces of the tunnel lining surface according to the each span.

Means to Solve the Problem

The first invention is characterized with a tunnel lining surface inspection system wherein, while a vehicle is travelling in a tunnel, a tunnel lining surface image is photographed by photography means mounted in the vehicle and is processed into an image used for inspecting the tunnel lining surface, the system comprising photography means mounted in the vehicle, having a photography range of one side face in both side faces of the tunnel lining surface, fixing/reversing means for fixing the photography means to a first photography position where the one side face in the both side faces of the tunnel lining surface can be photographed and for reversing the photography means to fix the photography means to a second photography position where the other side face in the both side faces of the tunnel lining surface can be photographed, and image processing means for comparing a first image showing the one side face in the both side faces of the tunnel lining surface and a second image showing the other side face in the both side faces of the tunnel lining surface, indicating portions forming an identical span of the tunnel lining surface, and thereby, synthesizing the images of the each area into an image showing the both sides of the tunnel lining surface for each span of the tunnel lining surface, the first image having been photographed by the photography means while the photography means being fixed to the first photography position and the second image having been photographied by the photography means while the photography means being fixed to the second photography position.

The second invention is characterized, in the first invention, in that the tunnel lining surface inspection system wherein the photography means comprises a plurality of line sensors which are arranged along a circumferential direction of the tunnel lining surface and photography images of each area along the circumferential direction of the tunnel lining surface, and the image processing means compares the images of the each area having been photographed by the plurality of line sensors while the plurality of line sensors being fixed to the first photography position and the images of the each area having been photographed by the plurality of line sensors while the plurality of line sensors being fixed to the second photography position, indicates the portions forming the identical span of the tunnel lining surface, and thereby synthesizes the images of the each area into the image showing the both sides of the tunnel lining surface for the each span of the tunnel lining surface.

The third invention is characterized, in the first or second invention, in that the tunnel lining surface inspection system wherein the photography means comprises the plurality of line sensors which are arranged along the circumferential direction of the tunnel lining surface and photography images of the each area along the circumferential direction of the tunnel lining surface, and the fixing/reversing means comprises L-shaped member which is 90° rotatable around a drive axis in the circumferential direction of the tunnel lining surface and in which the plurality of line sensors are arranged along the circumferential direction of the tunnel lining surface and positioning means for positioning the L-shaped member in the first photography position and, when the L-shaped member is 90° rotated in the circumferential direction of the tunnel lining surface and positioned in the second photography position, positioning the L-shaped member in the second photography position.

The fourth invention is characterized with a vehicle used for a tunnel lining surface inspection system comprising
  photography means having a photography range of at least one side face in both side faces of a tunnel lining surface, the photography means comprising a plurality of line sensors which are arranged along a circumferential direction of the tunnel lining surface and photography images of each area along the circumferential direction of the tunnel lining surface, and
  fixing/reversing means for fixing the photography means to a first photography position where one side face in the both side faces of the tunnel lining surface can be photographied and for reversing the photography means to fix the photography means to a second photography position where the other side face in the both side faces of the tunnel lining surface can be photographied, the fixing/reversing means comprising
    L-shaped member which is 90° rotatable around a drive axis in the circumferential direction of the tunnel lining surface and in which the plurality of line sensors are arranged along the circumferential direction of the tunnel lining surface and
    positioning means for positioning the L-shaped member in the first photography position and, when the L-shaped member is 90° rotated in the circumferential direction of the tunnel lining surface and positioned in the second photography position, positioning the L-shaped member in the second photography position.

Effect of the Invention

According to the present invention, driving the vehicle mounted with the photography means having the photography range of one side face in both side faces of the tunnel lining surface enables the images of both side faces of the tunnel lining surface to be obtained. According to the present invention, the images showing both side faces of the tunnel lining surface can be obtained according to each span.

Thereby, according to each span, the soundness (degree of deterioration) of the tunnel lining surface can be inspected, and according to each span, the inspection result can be managed.

BRIEF EXPLANATION OF THE DRAWINGS

FIG. 12 (a), (b), (c) explains an image processing for distortion correction (FIG. 10 (b)).

Description of the reference numerals

Figure 1:
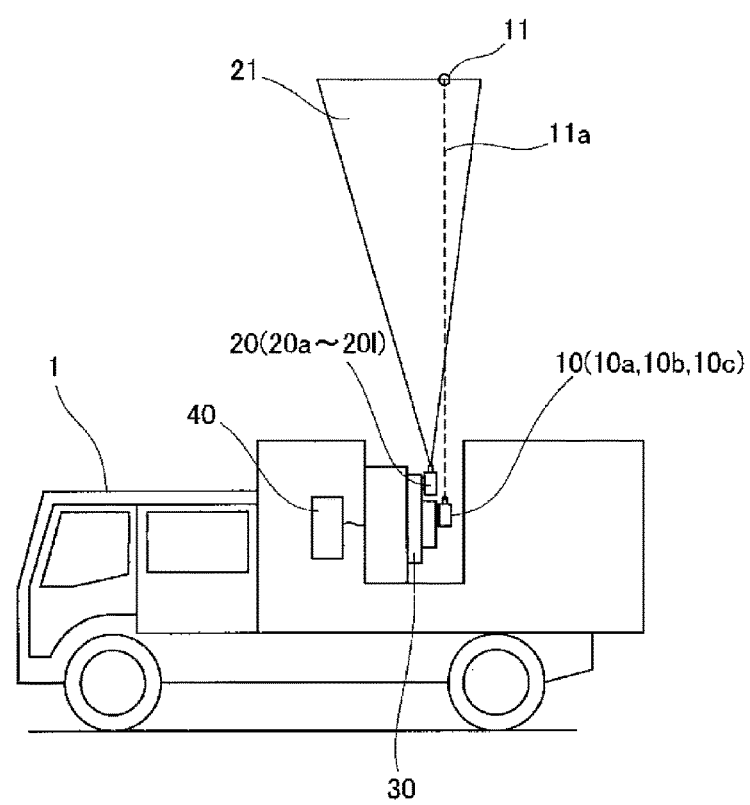
FIG. 1 shows the left side face of the vehicle used for the tunnel lining surface inspection system in the present invention.

1 Vehicle  10 Photography means  20 Illumination means
30 Fixing/reversing means  32 L-shaped member  34 Positioning means
100 Tunnel lining surface S (S 1, S 2, S 3 . . . Sn) span
110-1, 110-2, 110-3 . . . 110-n Synthesized images

BEST EMBODIMENTS FOR IMPLEMENTING THE INVENTION

The embodiment of the tunnel lining surface inspection system and the vehicle used for the tunnel lining surface inspection system in the present invention is explained below, while referring to the drawings.

FIG. 1 shows the left side face of the vehicle 1 used for the tunnel lining surface inspection system in the present invention.

The vehicle 1 is a work vehicle with a base of work track used for road maintenance work, for example.

The loading space of the vehicle 1 has a container shape, and the door of one side face of the container (the left side face in FIG. 1) and the door at the ceiling of the container are openable. FIG. 1 shows the state where the doors are opened.

The photography means 10 and the illumination means 20 are arranged in the loading space of the vehicle 1 so that, when the above doors in the vehicle 1 are opened, the tunnel lining surface can be photographied and illuminated.

A line sensor (camera) is assumed as the photography means 10. In the embodiment, three line sensors 10 a, 10 b, 10 c are assumed. When the three line sensors 10 a, 10 b, 10 c are comprehensively described, they are dubbed line sensors 10, hereinafter.

A halogen lamp is assumed as the illumination means 20. A metal halide lamp (HID) and LED lighting may be used as a light source, as well. In the embodiment, twelve halogen lamps 20 *a*, 20 *b*, 20 *c*, 20 *d*, 20 *e*, 20 *f*, 20 *g*, 20 *h*, 20 *i*, 20 *j*, 20 *k*, 20 *l* are assumed. When the twelve halogen lamps 20 *a*-20 *l* are comprehensively described, they are dubbed halogen lamps 20, hereinafter.

The line sensors 10 are fixed to the fixing/reversing means 30 so that the direction vertical to the travel direction of the vehicle 1 is the direction of the collimation line 11 *a*. The line sensors 10 photography the photography range 11 with the predetermined picture angle spreading toward the depth direction and the spectator direction to the drawing of FIG. 1.

The halogen lamps 20 are fixed to the fixing/reversing means 30 so as to project light in the direction vertical to the travel direction of the vehicle 1. The line sensors 10 and the halogen lamps 20 are positioned so that the emission range 21 of the halogen lamps 20 includes the collimation line 11 *a* of the line sensors 10.

The image processing unit 40 receives the imaging data photographied by the line sensors 10 and performs image processing to generate the tunnel lining surface images.

Figure 2:
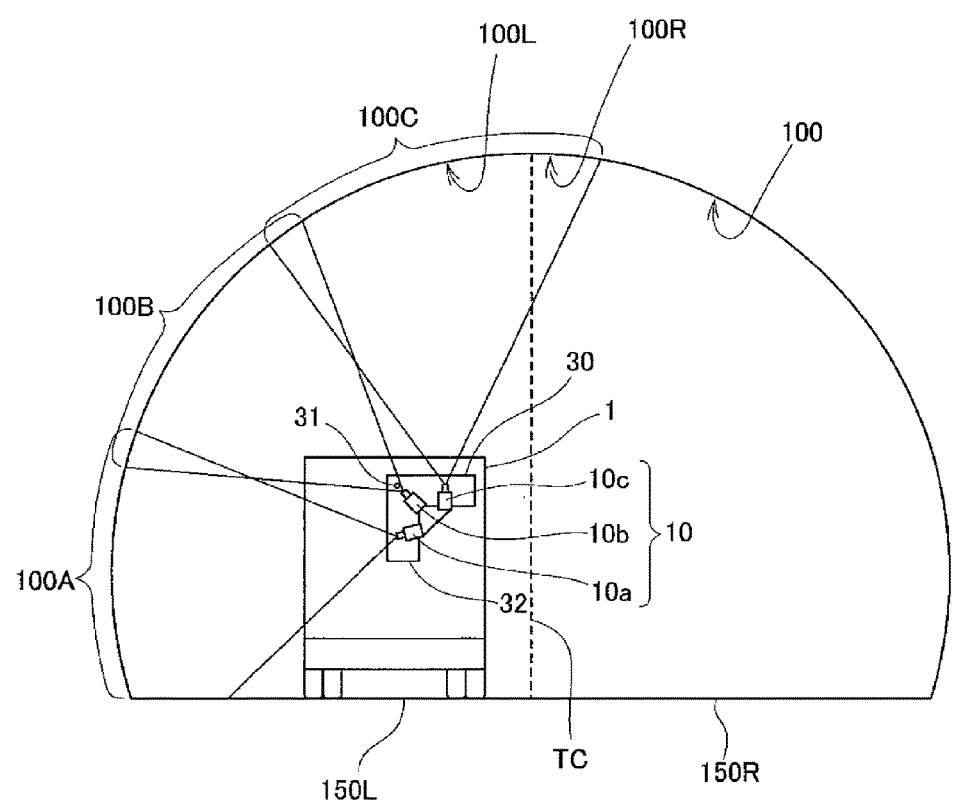
FIG. 2 is a cross section plan showing the state where the vehicle is traveling on the traveling lane on the left side in the tunnel and shows how the tunnel lining surface is photographied by using the line sensors and the halogen lamps.

FIG. 2 is a cross section plan showing the state where the vehicle 1 is traveling on the traveling lane 150 L on the left side in the tunnel and shows how the tunnel lining surface 100 is photographied by using the line sensors 10 and the halogen lamps 20. For convenience sake of explanation, the road surface on the left side of the center line TC in the tunnel in the drawing is defined as the traveling lane on the left 150 L, and the road surface on the right side of the center line TC in the tunnel in the drawing is dubbed as the overtaking lane on the right 150 R. Also, the left side of the tunnel lining surface 100, delimited by the center line TC of the tunnel is defined as the left side face 100 L, and the right side of the tunnel lining surface 100, delimited by the center line TC of the tunnel is defined as the right side face 100 R.

As shown in FIG. 2, the photography means 10 has the photograph range of at least one side face (left side face 100 L in FIG. 2) in the both side faces 100 L, 100 R of the tunnel lining surface 100, and is configured to comprise a plurality of (three in the embodiment) line sensors 10 *a*, 10 *b*, 10 *c* which are arranged along a circumferential direction of the tunnel lining surface 100 and photography each area 100 A, 100 B, 100 C along the circumferential direction of the tunnel lining surface 100. The line sensors 10 *a*, 10 *b*, 10 *c* respectively have the picture angle of 61°. Therefore, in the each area 100 A, 100 B, 100 C, the neighboring areas are partially overlapped.

As mentioned below in FIG. 4 (not shown in FIG. 2), the illumination means 20 has the emission range of at least one side face (left side face 100 L in FIG. 2) of the both side faces 100 L, 100 R of the tunnel lining surface 100 and is configured to comprise a plurality of (twelve in the embodiment) halogen lamps 20 *a*-20 *l* which are arranged along a circumferential direction of the tunnel lining surface 100 and illuminate the each area 100 A, 100 B, 100 C along the circumferential direction of the tunnel lining surface 100 (see FIG. 4).

The fixing/reversing means 30 fixes the photography means 10 to a first photography position where the left side face 100 L, namely the one side face in both side faces of the tunnel lining surface 100 can be photographied, and reverses the photography means 10 to fix the photography means 10 to a second photography position where the right side face 100 R, namely the other side face in both side faces of the tunnel lining surface 100 can be photographied, the fixing/reversing means 30 being configured to comprise the L-shaped member 32 which is 90° rotatable around the drive axis 31 in the circumferential direction of the tunnel lining surface 100 and in which a plurality of (three in FIG. 2) line sensors 10 *a*, 10 *b*, 10 *c* are arranged along the circumferential direction of the tunnel lining surface 100 and the positioning means (not shown in FIG. 2 and mentioned below in FIG. 4) for positioning this L-shaped member 32 in the first photography position and, when the L-shaped member 32 is 90° rotated in the circumferential direction of the tunnel lining surface 100 and positioned in the second photography position, positioning the L-shaped member 32 in this second photography position.

When the fixing/reversing means 30 is positioned in the first photography position, the illumination means 20 is similarly positioned in the first photography position and illuminates the photography area 100 A, 100 B, 100 C, corresponding to the first photography position, and, when the fixing/reversing means 30 is positioned in the second photography position, the illumination means 20 is similarly positioned in the second photography position and illuminates the photography area 100 D, 100 E, 100 F (see FIG. 3), corresponding to the second photography position.

Figure 3:
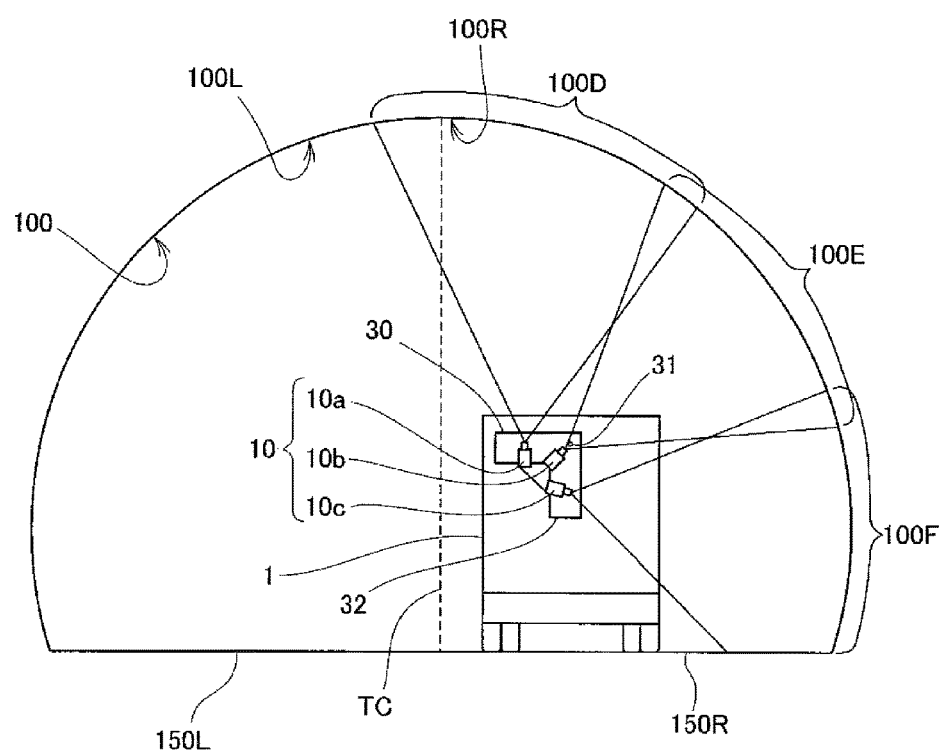
FIG. 3 corresponds to FIG. 2 and is a cross section plan showing the state where the vehicle is traveling on the overtaking lane on the right side in the tunnel.

FIG. 3 corresponds to FIG. 2 and is a cross section plan showing the state where the vehicle 1 is traveling on the overtaking lane on the right side 150 R in the tunnel.

FIG. 3 shows the state in which the photography means 10 and the illumination means 20 are positioned in and fixed to the second photography position by being 90° reversed clockwise from the first photography position (FIG. 2) by the fixing/reversing means 30.

As shown in FIG. 3, the photography means 10 photographies the right side face 100 R of the tunnel lining surface 100, namely, the line sensors 10 *a*, 10 *b*, 10 *c* respectively photography each area 100 D, 100 E, 100 F along the circumferential direction of the tunnel lining surface 100.

The illumination means 20 illuminates the right side face 100 R of the tunnel lining surface 100, namely, the twelve halogen lamps 20 *a*-20 *l* emit light to each area 100 D, 100 E, 100 F along the circumferential direction of the tunnel lining surface 100.

Figure 4:
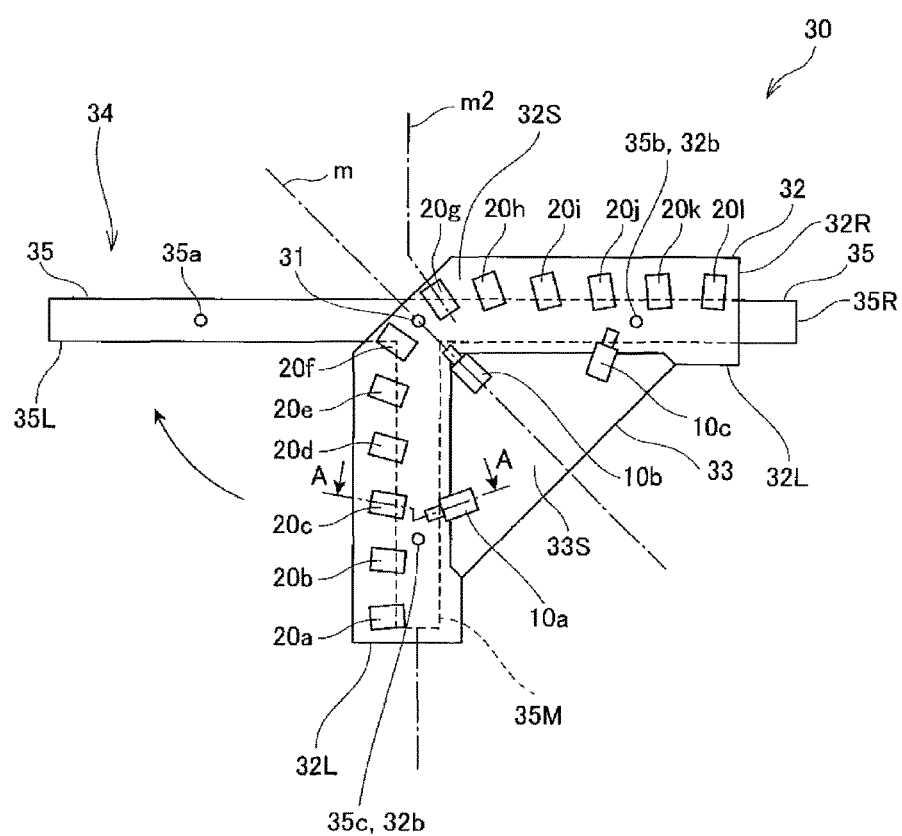
FIG. 4 planarly shows how the fixing/reversing means is configured.

FIG. 4 planarly shows how the fixing/reversing means 30 is configured.

The L-shaped member 32 has the arms 32 L, 32 R respectively having the same length and being symmetrical to the symmetry axis m 1 which passes the drive axis 31 as the rotation center, and is integrally formed with the arms 32 L, 32 R vertically crossed to each other, and the twelve halogen lamps 20 *a*-20 *l* are symmetrically arranged on the upper face 32 S of the L-shaped member 32.

The triangle-shaped stage member 33 is arranged at the inside corner of the L-shaped member 32 so as to be symmetrical to the symmetry axis m 1. The three line sensors 10 *a*, 10 *b*, 10 *c* are arranged so as to be symmetrical to the symmetry axis m 1 on the upper face 33 S of the stage member 33. The positioning means 34 is configured to comprise the T-shaped member 35. The T-shaped member 35 is fixed to the frame installed in the loading space of the vehicle 1. The L-shaped member 32 is pivoted around the drive axis 31 relatively to the T-shaped member 35 fixed to the frame. The drive axis 31 is driven by drive means such as a motor not shown.

The T-shaped member 35 is symmetrical to the symmetry axis m 2 which passes the drive axis 31, and is integrally formed with the arms 35 L, 35 R, 35 M respectively having the same length from the drive axis 31 to the edge vertically crossed to each other, and on the arms 35 L, 35 R, 35 M, the holes 35 *a*, 35 *b*, 35 *c* having the same distance from the drive axis 31 are formed respectively.

On the arms 32 L, 32 R of the L-shaped member 32, the holes 32 *a*, 32 *b* having the same distance from the drive axis M are formed.

FIG. 4 shows the state where the photography means 10 is fixed to the first photography position.

The arm 35 M of the T-shaped member 35 and the arm 32 L of the L-shaped member 32 overlap, thereby the hole 35 *c* and the hole 32 *a* occupy the same position, and the arm 35 R of the T-shaped member 35 and the arm 32 R of the L-shaped member 32 overlap, thereby the hole 35 *b* and the hole 32 *b* occupy the same position. In this state, the pin not shown is inserted into the hole 35 *c* and the hole 32 *a*, and the pin not shown is inserted into the hole 35 *b* and the hole 32 *b*, thereby the photography means 10 and the illumination means 20 are fixed to the first photography position.

Figure 5:
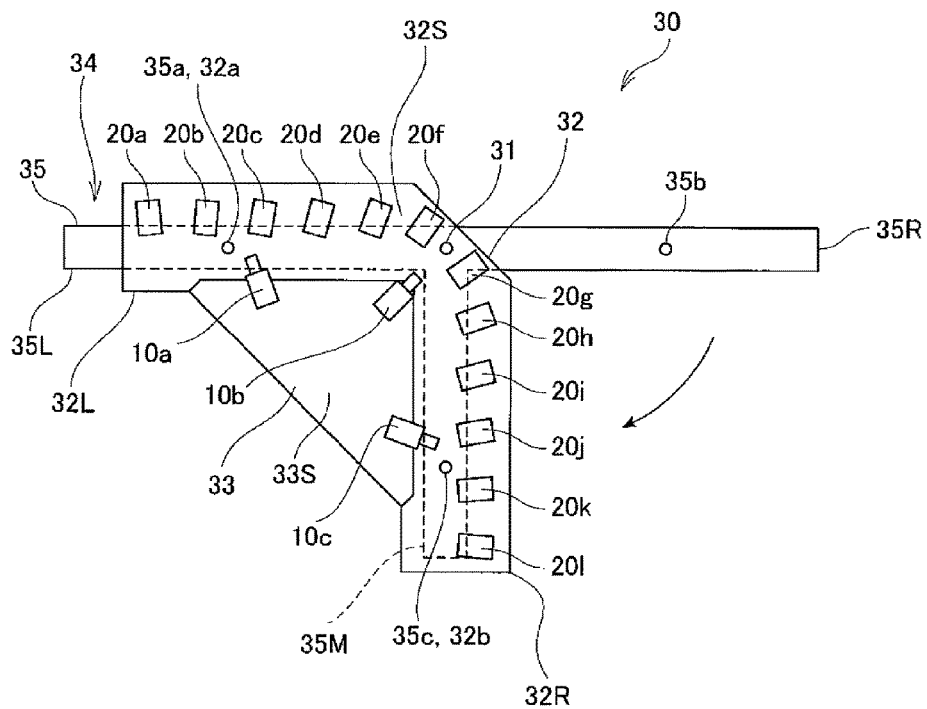
FIG. 5 shows the state where the photography means is fixed to the second photography position.

FIG. 5 shows the state where the photography means 10 is fixed to the second photography position.

As shown by the arrow in FIGS. 4, 5, when the L-shaped member 32 is 90° rotated clockwise by the drive axis 31, from the state shown in FIG. 4, the arm 35 L of the T-shaped member 35 and the arm 32 L of the L-shaped member 32 overlap, thereby the hole 35 *a* and the hole 32 *a* occupy the same position, and the arm 35 M of the T-shaped member 35 and the arm 32 R of the L-shaped member 32 overlap, thereby the hole 35 *c* and the hole 32 *b* occupying the same position. In this state, the pin not shown is inserted into the hole 35 *a* and the hole 32 *a*, and the pin not shown is inserted into the hole 35 *c* and the hole 32 *b*, thereby the photography means 10 and the illumination means 20 are fixed to the second photography position.

Figure 6:
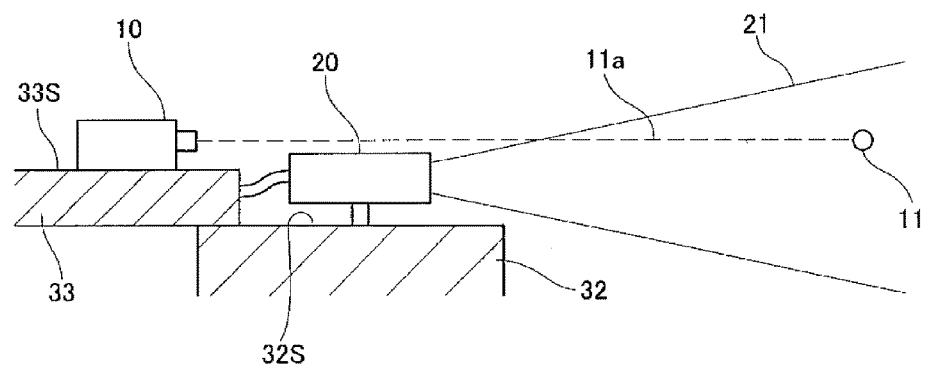
FIG. 6 shows a cross section of the stage member and the L-shaped member, and also shows an arrow guiding A-A cross section in FIG. 4.

FIG. 6 shows the cross section of the stage member 33 and the L-shaped member 32, and the arrow guiding A-A cross section in FIG. 4. The upper face 33 S of the stage member 33 is arranged in a position higher than the upper face 32 S of the L-shaped member 32. Therefore, the line sensors 10 are installed higher than the halogen lamps 20.

Here, the line sensors 10 and the halogen lamps 20 are positioned so that the emission range 21 of the halogen lamps 20 includes the collimation line 11 *a* of the line sensors 10 but does not interfere with the halogen lamps 20, etc. It is noted that the picture angle 11 of the line sensors 10 spreads toward the depth direction and the spectator direction in FIG. 6.

Figure 7:
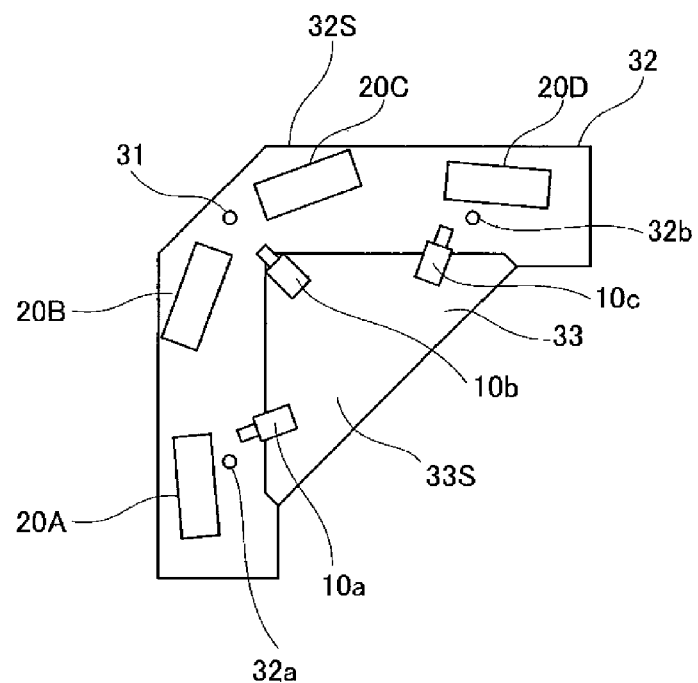
FIG. 7 corresponds to FIG. 4, showing a transformation example in which, as the illumination means arranged in the L-shaped member, the halogen lamps are replaced with LED unit.

FIG. 7 corresponds to FIG. 4, showing a transformation example in which, as the illumination means 20 arranged in the L-shaped member 32, the halogen lamps 20 are replaced with LED unit 20. In other words, on the upper face 32 S of the L-shaped member 32, four LED units 20 A, 20 B, 20 C, 20 D are allocated so as to be symmetrical. The four LED units 20 A, 20 B, 20 C, 20 D have the same emission range 21 as the halogen lamps 20 *a*-20 *l*.

Figure 8:
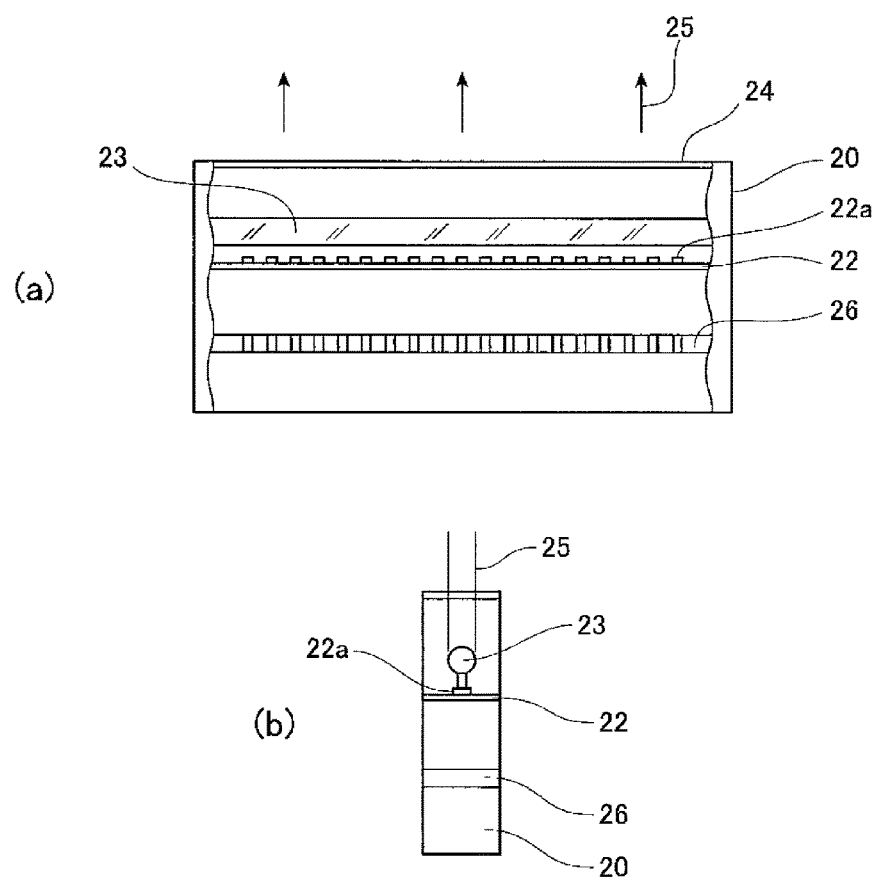
FIG. 8 shows an internal configuration of LED unit, FIG. 8 (a) being a cross section plan showing the inside in the state shown in FIG. 7, and FIG. 8 (b) being a vertical section plan.

FIG. 8 shows the internal configuration of LED unit 20, FIG. 8 (*a*) being a cross section plan seen at the above surface in FIG. 7, and FIG. 8 (*b*) being a vertical section plan seen as a section of FIG. 7.

The LED unit 20 is configured to comprise a line-shaped LED substrate 22 where a plurality of LED 22 *a* are arranged along a circumferential direction of the tunnel lining surface 100 (the direction vertical to the travel direction of the vehicle 1), a cylinder-shaped rod lens 23 which refracts the light emitted by the line-shaped LED substrate 22, the lens 23 having the longitudinal length corresponding to the LED arrangement length of the line-shaped LED substrate 22, a cover glass 24 which transmits and emits outside the light refracted by the rod lens 23, and a fan 26 for cooling the line-shaped LED substrate 22.

The above embodiment is explained based on the assumption that the photography means 10 is configured with three line sensors 10 *a*, 10 *b*, 10 *c*, but the configuration with more photography means or one photography means may be accepted. For example, the embodiment in which one line sensor 20 having the photography range where one side face of the tunnel lining surface 100 can be photographied installed in the fixing/reversing means 30 photoghraphies the left side face 100 L at the first photography position, and then is 90° reversed and photoghraphies the right side face 100 R at the second photography position, thereby both side faces 100 L, 100 R of the tunnel lining surface 100 are photographied by the one line sensor 20 is possible, as well.

Figure 9:
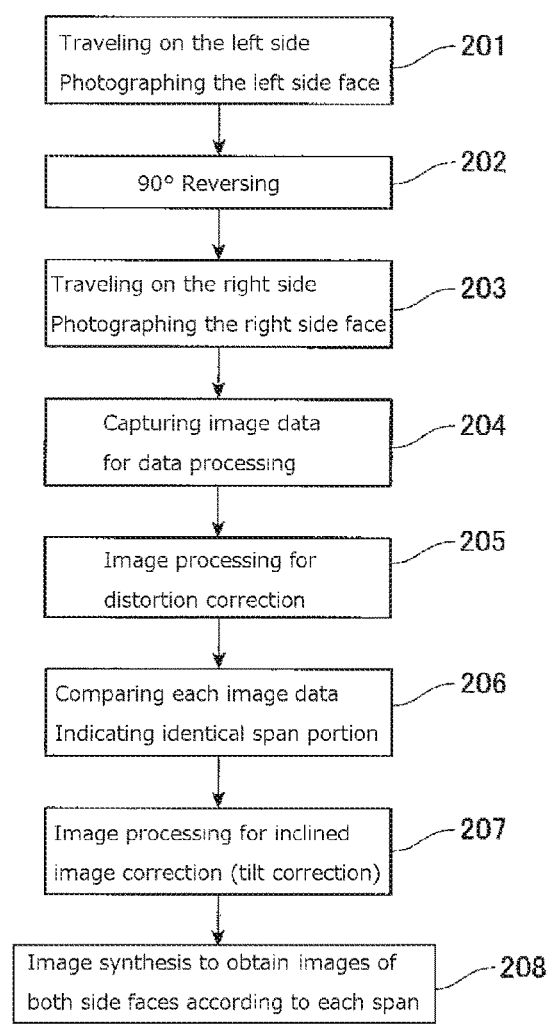
FIG. 9 shows a procedure of the processing performed in the tunnel lining surface inspection system in the embodiment.

FIG. 9 shows the procedure of the processing performed in the tunnel lining surface inspection system in the embodiment.

At first, while the line sensors 10 *a*, 10 *b*, 10 *c* and the halogen lamps 20 *a*-20 *l* are fixed to the first photography position, the vehicle 1 drives along the traveling lane 150 L on the left side. While the vehicle 1 is traveling, the three line sensors 10 *a*, 10 *b*, 10 *c* and the halogen lamps 20 *a*-20 *l* are activated. Thereby, each area 100 A, 100 B, 100 C of the left side face 100 L of the tunnel lining surface 100 is sequentially photographied by the three line sensors 10 *a*, 10 *b*, 10 *c*. The image data of the each area 100 A, 100 B, 100 C of the left side face 100 L of the tunnel lining surface 100 photographied by the each line sensor 10 *a*, 10 *b*, 10 *c* are captured into the image processing unit 40. (See FIG. 2; Step 201).

Then, the fixing/reversing means 30 90° reverses the line sensors 10 *a*, 10 *b*, 10 *c* and the halogen lamps 20 *a*-20 *l* (Step 202).

While the line sensors 10 *a*, 10 *b*, 10 *c* and the halogen lamps 20 *a*-20 *l* are fixed to the second photography position, the vehicle 1 drives along the overtaking lane 150 R on the right side.

While the vehicle 1 is traveling, the three line sensors 10 *a*, 10 *b*, 10 *c* and the halogen lamps 20 *a*-20 *l* are activated. Thereby, each area 100 D, 100 E, 100 F of the right side face 100 R of the tunnel lining surface 100 is sequentially photographied by the three line sensors 10 *a*, 10 *b*, 10 *c*. The image data of the each area 100 D, 100 E, 100 F of the right side face 100 R of the tunnel lining surface 100 photographied by the each line sensor 10 *a*, 10 *b*, 10 *c* are captured into the image processing unit 40. (See FIG. 3; Step 203).

The image data of the each area 100 A, 100 B, 100 C of the left side face 100 L of the tunnel lining surface 100 and the image data of the each area 100 D, 100 E, 100 F of the right side face 100 R of the tunnel lining surface 100, captured into the image processing unit 40 are captured into the exterior personal computer, for example, for image processing (Step 204).

Next, the image processing for distortion correction mentioned below is performed (Step 205).

Next, the portions forming the identical span S of the tunnel lining surface 100 are indicated by comparing the images of the each area 100 A, 100 B, 100 C, 100 D, 100 E, 100 F, having been photographied by the three line sensors 10 *a*, 10 *b*, 10 *c* (Step 206), as mentioned below.

Next, the image processing for inclined image correction (tilt correction) mentioned below is performed (Step 207).

Next, the image synthesis processing is performed to obtain the images 110-1, 110-2, . . . 110-*n* showing both side faces 100 L, 100 R of the tunnel lining surface 100 according to the each span S 1, S 2 . . . S n of the tunnel lining surface 100 (Step 208).

Figure 10:
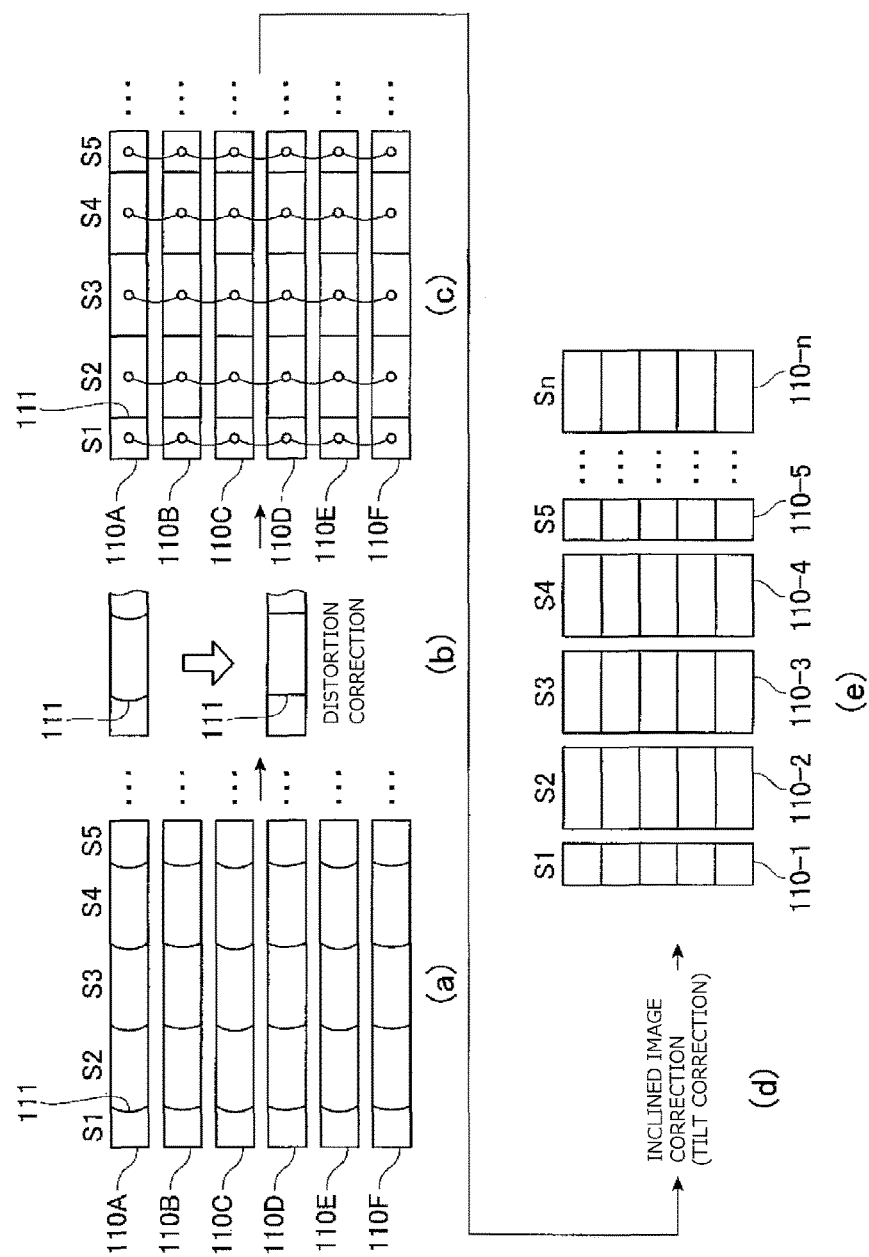
FIG. 10 (a), (b), (c), (d), (e) explains an image processing performed in the personal computer.

FIG. 10 explains the image processing performed in the personal computer.

To be specific, each image 110 A, 110 B, 110 C, 110 D, 110 E, 110 F showing each area 100 A, 100 B, 100 C, 100 D, 100 E, 100 F of the left side face 100 L and the right side face 100 R of the tunnel lining surface 100 is captured (FIG. 10 (a)), the image processing for distortion correction is performed to the each image 110 A, 110 B, 110 C, 110 D, 110 E, 110 F (FIG. 10 (b)), and the each image 110 A, 110 B, 110 C, 110 D, 110 E, 110 F is compared to indicate the portions forming the identical span S of the tunnel lining surface 100 (FIG. 10 (c)), the image processing for inclined image correction (tilt correction) is performed (FIG. 10 (d)), and the image synthesis processing is performed to obtain the images 110-1, 110-2, . . . 110-n showing both side faces 100 L, 100 R of the tunnel lining surface 100 according to each span S 1, S 2 . . . S n of the tunnel lining surface 100 (FIG. 10 (e)).

Figure 11:
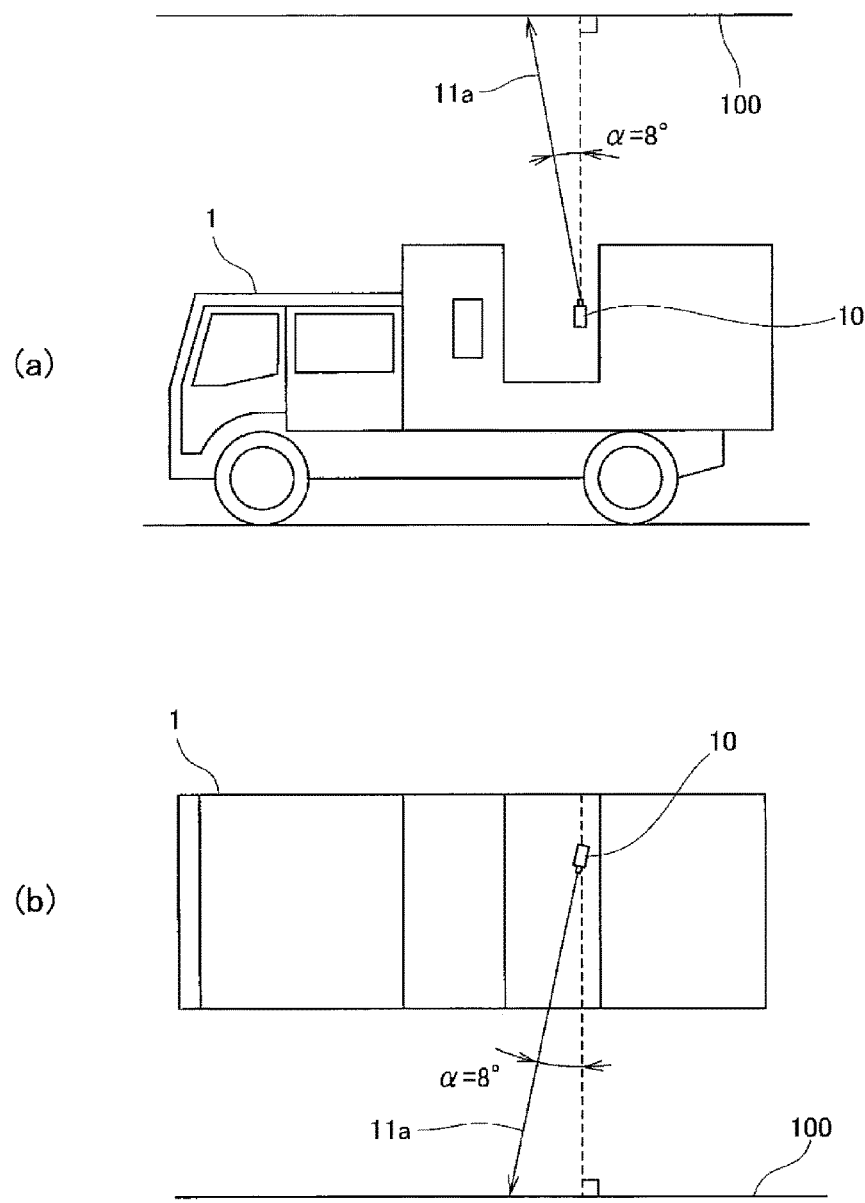
FIG. 11 (a), (b) explains an image processing for distortion correction (FIG. 10 (b)).

FIGS. 11, 12 explain the image processing for distortion correction (FIG. 10 (b)).

When the photography means 10 is arranged so that the collimation of the photography means 10 crosses the tunnel lining surface 100 at right angles and dew such as water drops is formed on the surface of the tunnel lining surface 100, it is likely that the positional relation of the illumination means 20 and the photography means 10 causes the dew to regularly reflect and partially appear on the image phtographied by the photography means 10 and makes it difficult to identify the defect such as cracking to be appropriately photographied. Therefore, for the purpose of avoiding this, it is effective to incline the axis of emission direction of the illumination means 20 and the axis of the photography direction (collimation) of the photography means 10.

To be specific, the photography means (line sensor) 10 is arranged so that, the collimation line 11 a of the photography means (line sensor) 10 is inclined forward by the angle α (8°, for example) to the vertical direction, namely the direction vertical to the ceiling face of the tunnel lining surface 100, seen from the side face of the vehicle 1, as shown in FIG. 11 (a), and the collimation line 11 a of the photography means (line sensor) 10 is inclined forward by the angle α (8°, for example) to the horizontal direction, namely the direction vertical to the side face of the tunnel lining surface 100, seen from the upper face of the vehicle 1, as shown in FIG. 11 (b).

The emission direction of the illumination means (halogen lamp) 20 is similarly inclined.

FIG. 12 (a) shows how the collimation line 11 a of the photography means (line sensor) 10 and the joint 111 of the tunnel lining surface 100 are related to each other. The joint vertical to the travel direction of the vehicle 1 (direction of the center line TC in the tunnel) divides each span S 1, S 2 . . . of the tunnel lining surface 100.

As mentioned above, inclining the axis of the emission direction of the illumination means 20 and the axis (collimation) of the photography direction of the photography means 10 causes the direction of the collimation line 11 a and the direction of the joint 111 to be crossed at the predetermined angle β and, since the collimation line 11 a passes the joint 111 in a different timing according to each image pixel, the joint 111 in the images photographied by the photography means (line sensors) 10 gets distorted in a curved form (FIG. 12 (b)).

Therefore, the image processing is performed to correct the joint 111 distorted in the photographied image to be in its original linear-shape (FIG. 12 (c)).

Figure 13:
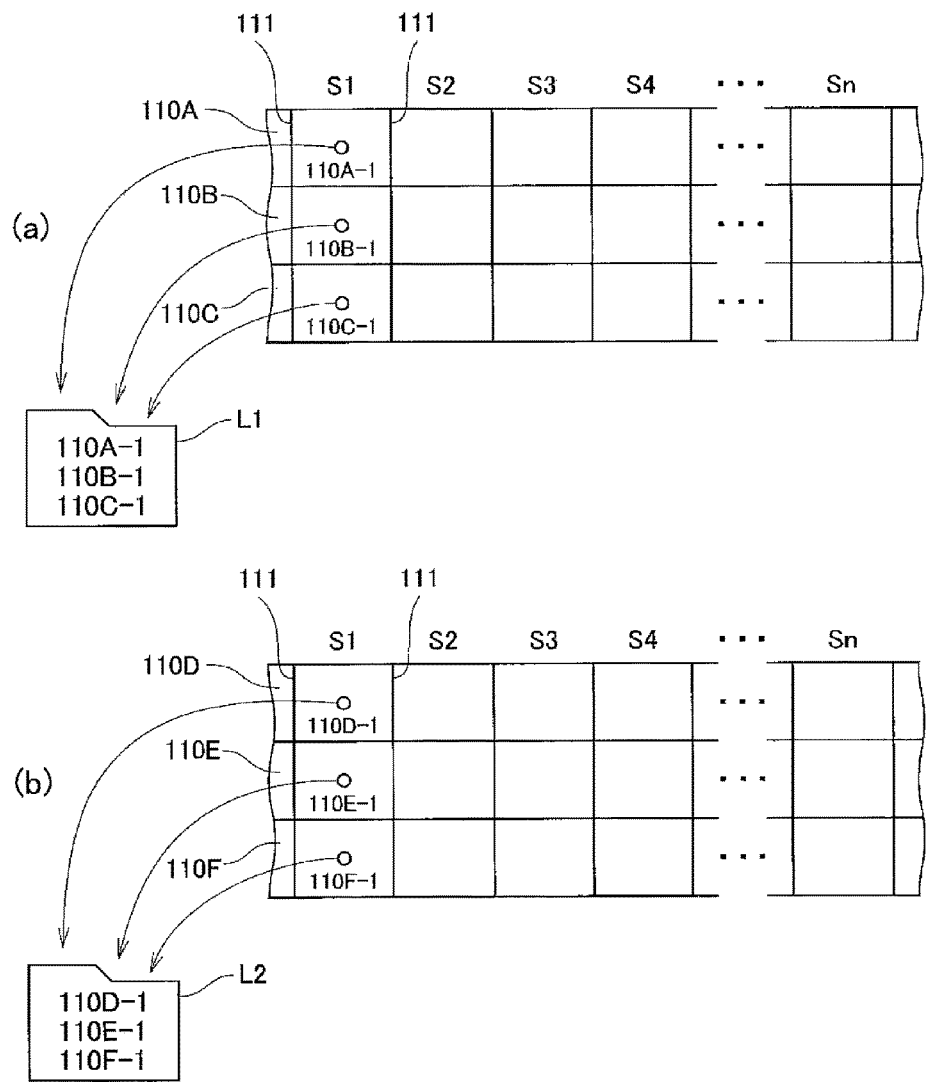
FIG. 13 explains an processing (FIG. 10 (c)) for indicating the portions forming the identical span of the tunnel lining surface by comparing the each image.

FIG. 13 explains the processing (FIG. 10 (c)) for indicating the portions forming the identical span S of the tunnel lining surface 100 by comparing the each image 110 A-110 F.

This processing is performed on the basis of the joint 111 returned to be linear shaped by the image processing for distortion correction.

As shown in FIG. 13 (a), the each image 110 A, 110 B, 110 C obtained with respect to the left side face 100 L of the tunnel lining surface 100 is placed on the display of the personal computer so as to occupy the same position. The position is matched on the basis of the joint 111 returned to be linear shaped.

Since the shutters of the each line sensor 10 a, 10 b, 10 c are activated almost at the same time, the joint 111 of the each image 110 A, 110 B, 110 C occupies almost the same position on the display. On the tunnel lining surface 100, each position is identified by KP (kilo post), span number (lining number), illumination number, etc., which are photographied in the each image, and thus, the positions may be recognized based on them.

Next, from among the each image 110 A, 110 B, 110 C, the portions forming the identical span S of the tunnel lining surface 100 are indicated. For example, among the each image 110 A, 110 B, 110 C, if the portions which are to form the span S 1 are identified respectively as 110 A-1, 110 B-1, 110 C-1 (to be used as the reference numerals for representing the image data of span S 1, hereinafter), the image data 110 A-1, 110 B-1, 110 C-1 which identify the portions 110 A-1, 110 B-1, 110 C-1 which form the identical span S 1 are stored in the folder L 1 of Lane 1 (traveling lane 150 L) while being associated with the address showing the span S 1. Similarly, the portions forming the identical span S 2, S 3 . . . S n are indicated, and the image data which identify the portions which form the identical span S 2, S 3 . . . S n are stored in the folder L 1 of Lane 1 (traveling lane 150 L).

The similar processing is performed for the overtaking lane 150 R. To be specific, as shown in FIG. 13 (b), among the each image 110 D, 110 E, 110 F, if the portions which are to form the span S 1 are identified respectively as 110 D-1, 110 E-1, 110 F-1 (to be used as the reference numerals for representing the image data of span S 1, hereinafter), the image data 110 D-1, 110 E-1, 110 F-1 which identify the portions 110 D-1, 110 E-1, 110 F-1 which form the identical span S 1 are stored in the folder L 2 of Lane 2 (overtaking lane 150 R) while being associated with the address showing the span S 1. Similarly, the portions forming the identical span S 2, S 3 . . . S n are indicated, and the image data which identify the portions which form the identical span S 2, S 3 . . . 5 n are stored in the folder L 2 of Lane 2 (overtaking lane 150 R).

Figure 14:
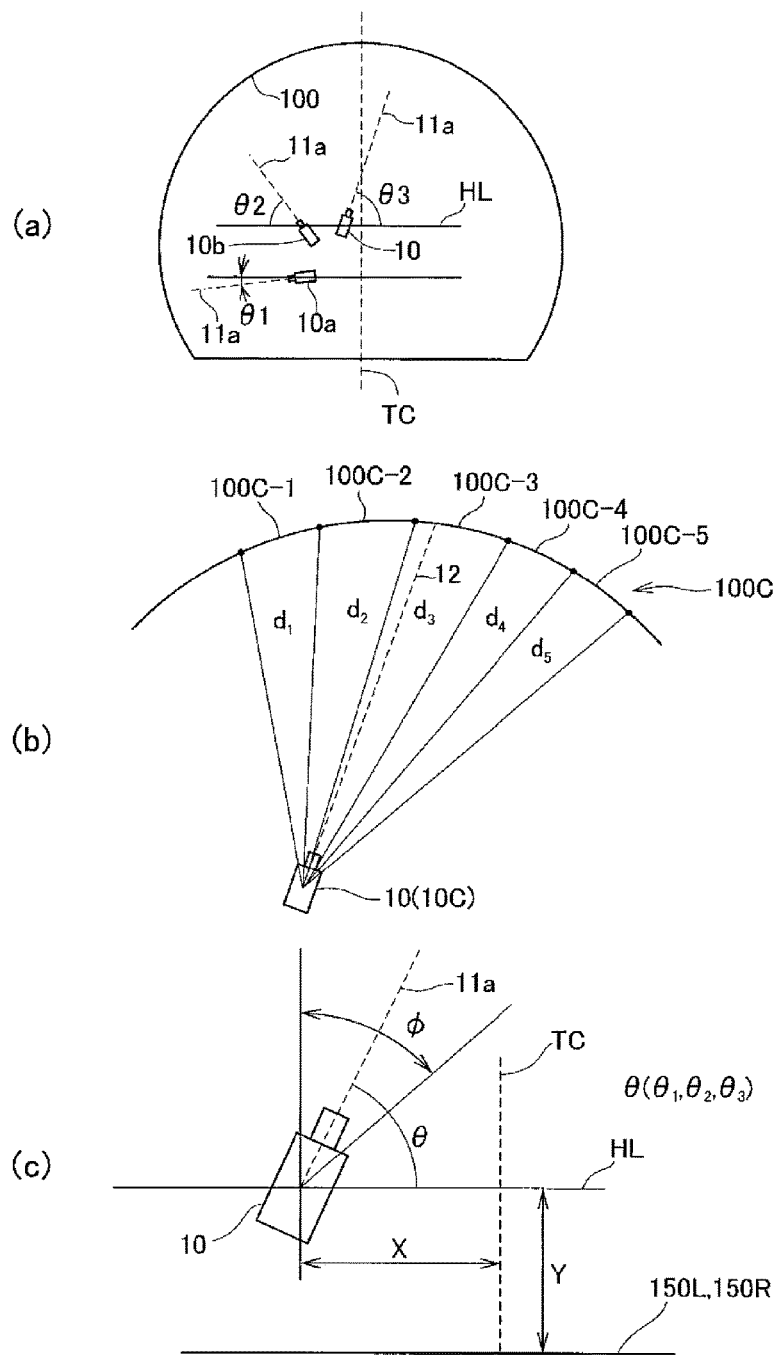
FIG. 14 (a) (b) (c) shows an image processing for inclined image correction (tilt correction) (FIG. 10 (d)).

FIG. 14 explains the image processing for inclined image correction (tilt correction) (FIG. 10 (d)).

FIG. 14 (a) shows the positional relation of the tunnel lining surface 100 and the line sensors 10 a, 10 b, 10 c.

The line sensors 10 a, 10 b, 10 c are positioned to be off set to the center line TC of the tunnel. Therefore, the collimation lines 11 a of the line sensors 10 a, 10 b, 10 c are not confronting the tunnel lining surface 100 as the photographing object face to face but inclined to it. Accordingly, the line sensors 10 a, 10 b, 10 c, photography the tunnel lining surface 100 situated near as larger images, and photography the tunnel lining surface 100 situated far as smaller images.

As shown in FIG. 14 (b), the area photographied by the line sensors 10 (line sensor 10 c, for example) are shown as 100 C, for example, and, among this photography area 100

C, to be specific among each divided area 100 C-1, 100 C-2, 100 C-3, 100 C-4, 100 C-5, the tunnel lining surface 100 is most largely photographied in the divided area 100 C-1 nearest to the line sensor 10 and the tunnel lining surface 100 is smallest photographied in the divided area 100 C-5 furthest from the line sensor 10.

Accordingly, the image processing is performed so that the tunnel lining surface 100 as the photographing object is photographied so as to be in the actual size in each area of the images.

The parameters for the line sensors 10 required for the image processing for inclined image correction (tilt correction) are given as mentioned below (see FIG. 14 (*c*)).

$\theta$: the angle showing the photography direction of the line sensor 10 (collimation line 11 *a*) (the angle to the horizontal line HL).

X: the position in the two dimensional horizontal direction of the line sensor 10 (lens, sensor) (the relative position on the basis of the center line TC of the tunnel).

Y: the position in the two dimensional vertical direction of the line sensor 10 (lens, sensor) (the relative position on the basis of the road surface 150 L, 150 R of the tunnel).

$\phi$: the picture angle of the line sensor 10.

Once the above parameters $\theta$, X, Y, $\phi$ are obtained and the data showing the shape of the tunnel are obtained from the CAD drawing, for example, the distances d 1, d 2, d 3, d 4, d 5 from the line sensor 10 to the tunnel lining surface 100 are gained according to the each divided area 100 C-1, 100 C-2, 100 C-3, 100 C-4, 100 C-5 in FIG. 14 ( b).

Then, the image processing is performed so that the tunnel lining surface 100 as the photographing object is photographied to be in the actual size in the each divided area 100 C-1, 100 C-2, 100 C-3, 100 C-4, 100 C-5, according to the gained distances d 1, d 2, d 3, d 4, d 5.

Figure 15:
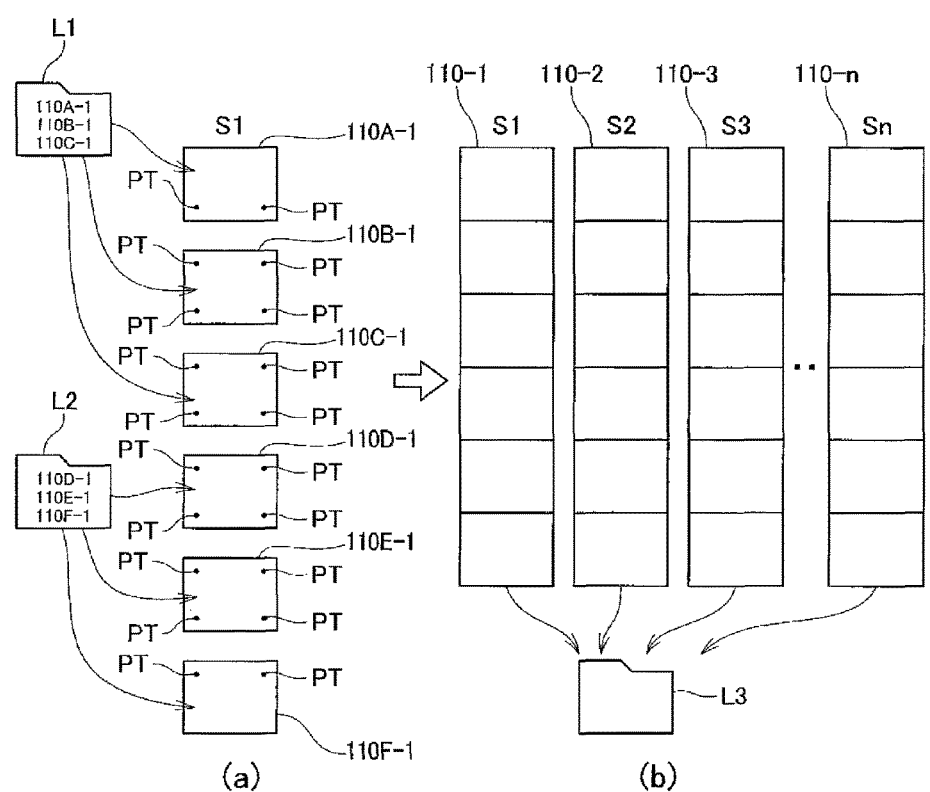
FIG. 15 (a) (b) explains an image synthesis processing (FIG. 10 (e)) for obtaining the images showing both side faces of the tunnel lining surface according to each span of the tunnel lining surface.

FIG. 15 explains the image synthesis processing (FIG. 10 (*e*)) for obtaining the images 110-1, 110-2, . . . 110-*n* showing both side faces 100 L, 100 R of the tunnel lining surface 100 according to the each span S 1, S 2 . . . S n of the tunnel lining surface 100.

As shown in FIG. 15 (a), the image data 110 A-1, 110 B-1, 110 C-1 associated with the address showing the span S 1 are read from the folder L 1 of Lane 1 (traveling lane 150 L). Similarly, the image data 110 D-1, 110 E-1, 110 F-1 associated with the address showing the span S 1 are read from the folder L 2 of Lane 2 (overtaking lane 150 R).

Next, on the display of the personal computer, with respect to the each image 110 A-1, 110 B-1, 110 C-1, 110 D-1, 110 E-1, 110 F-1, the corresponding points PT at which the neighboring images are combined to each other are indicated.

In the photographied images in each area 100 A, 100 B, 100 C, 100 D, 100 E, 100 F, the neighboring areas are partially overlapped. The corresponding points PT are indicated in consideration of the overlapping.

Thereby, as shown in FIG. 15 (b), the images 110 A-1, 110 B-1, 110 C-1, 110 D-1, 110 E-1, 110 F-1 are respectively synthesized on the basis of the corresponding points PT to obtain the image 110-1 of the both/left and right sides 100 L and 100 R with respect to the span S 1 of the tunnel lining surface 100.

The similar processing is performed for the span S 2, S 3 . . . S n, as well, and, as shown in FIG. 15 (b), the images 110-2, 110-3 . . . 110-*n* showing both side faces 100 L, 100 R of the tunnel lining surface 100 are obtained according to the each span S 2, S 3 . . . S n of the tunnel lining surface 100. Each of the images 110-2, 110-3 . . . 110-*n* is stored in the predetermined file L 3 and used for inspecting the soundness of the tunnel lining surface 100.

As mentioned above, according to the present embodiment, driving the vehicle 1 mounted with the photography means 10 having the photography range of one side face in both side faces 100 L, 100 R of the tunnel lining surface 100 enables the images of both side faces 100 L, 100 R of the tunnel lining surface 100 to be obtained. According to the present embodiment, the images 110-1, 110-2 . . . 110-*n* showing both side faces 100 L, 100 R of the tunnel lining surface 100 can be obtained according to the each span S 1, S 2 . . . Sn. Thereby, according to the each span S 1, S 2 . . . Sn, the soundness (degree of deterioration) of the tunnel lining surface 100 can be inspected, and according to the each span S 1, S 2 . . . Sn, the inspection result can be managed.

Figure 16:
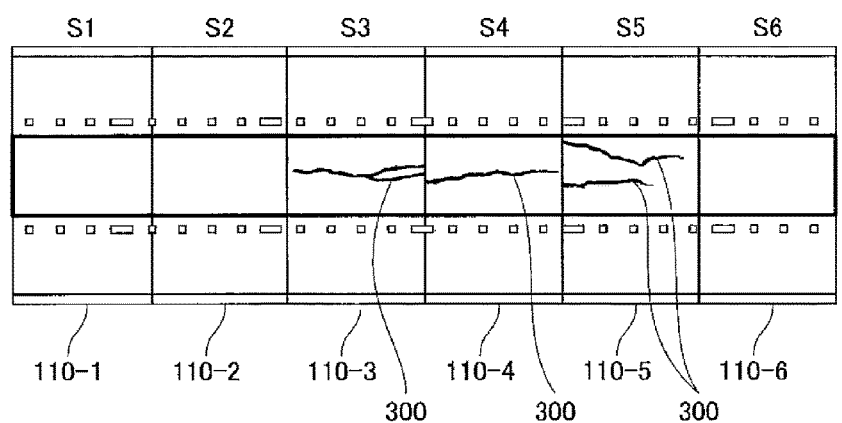
FIG. 16 shows an inspection example of the soundness (degree of deterioration) of the tunnel lining surface.

FIG. 16 shows the inspection example of the soundness (degree of deterioration) of the tunnel lining surface 100.

FIG. 16 shows the state in which the images 110-1, 110-2, 110-3, 110-4, 110-5, 110-6 of the each span S 1, S 2, S 3, S 4, S 5, S 6 are read from the file L 3 and sequentially displayed on the display of the personal computer. The operator, on the display, identifies the peelable cracking spot in the images of the tunnel lining surface 100 and draws the cracking 300.

Thereby, the width, length, direction, shape, density of the cracking 300 are extracted according to the each span S 1, S 2, S 3, S 4, S 5, S 6 and stored, while being associated with the image data 110-1, 110-2, 110-3, 110-4, 110-5, 110-6 of the each span S 1, S 2, S 3, S 4, S 5, S 6. Similarly, the occurring situation of abnormal situations such as presence of efflorescence may be extracted.

Therefore, according to the present embodiment, measures can be planned against the abnormal situations such as cracking according to the each span S 1, S 2, S 3, S 4, S 5, S 6.

It is noted that the above mentioned image processing performed on the personal computer may be performed semi-automatically, namely partially performed manually, and can be inevitably performed fully automatically.

The invention claimed is:

1. A tunnel lining surface inspection system wherein, while a vehicle is travelling in a tunnel, a tunnel lining surface image is photographed and is processed into an image used for inspecting the tunnel lining surface, the system comprising:

a plurality of line sensors mounted in the vehicle, having a photography range of one side face in both side faces of the tunnel lining surface, which photography images of each area along a circumferential direction of the tunnel lining surface, a fixing member mounted in a lodging space of the vehicle, on which the plurality of line sensors arranged along the circumferential direction of the tunnel lining surface and fixed so that the one side face in the both side faces of the tunnel lining surface can be photographed, a drive axis mounted in the fixing member for fixing the plurality of line sensors to a first photography position where one side face in the both side faces of the tunnel lining surface can be photographed and for fixing the plurality of line sensors to a second photography position where the other side face in the both side faces of the tunnel lining surface can be photographed, which rotates the fixing member in the circumferential direction of the tunnel lining surface, a first image processing unit capturing imaging data having been photographed by the plurality of line sensors, and a second image processing unit processing the imaging data having been captured in the first image processing unit, wherein the first image processing unit, while the plurality of line sensors being fixed in the first photography position after the drive axis being driven to the left and the fixing member being rotated to the left side in the circumferential direction of the tunnel lining surface, performs processing of capturing a first imaging data having been photographed by the plurality of line sensors, showing one side face in the both side faces of the tunnel lining surface, and, while the plurality of line sensors being fixed in the second photography position after the drive axis being driven to the right and the fixing member being rotated to the right side in the circumferential direction of the tunnel lining surface, performs processing of capturing a second imaging data having been photographed by the plurality of line sensors, showing the other side face in the both side faces of the tunnel lining surface, and the second image processing unit performs processing of selecting the imaging data forming the identical span of the tunnel lining surface in the first imaging data and the second imaging data according to each span of the tunnel lining surface, and performs image synthesis processing to obtain the images showing both side faces of the tunnel lining surface according to each span of the tunnel lining surface.

2. The tunnel lining surface inspection system claimed in claim 1 wherein the fixing member is L-shaped and 900 rotatable around the drive axis in the circumferential direction of the tunnel lining surface, the plurality of line sensors are arranged along the circumferential direction of the tunnel lining surface on the L-shaped member, and the drive axis is driven so that the L-shaped member is 900 rotated in the circumferential direction of the tunnel lining surface.

3. A vehicle used for a tunnel lining surface inspection system comprising a plurality of line sensors mounted in the vehicle, having a photography range of one side face in both side faces of the tunnel lining surface, which photography images of each area along a circumferential direction of the tunnel lining surface, a fixing member mounted in a lodging space of the vehicle, on which the plurality of line sensors arranged along the circumferential direction of the tunnel lining surface and fixed so that the one side face in the both side faces of the tunnel lining surface can be photographed, a drive axis mounted in the fixing member for fixing the plurality of line sensors to a first photography position where one side face in the both side faces of the tunnel lining surface can be photographed and for fixing the plurality of line sensors to a second photography position where the other side face in the both side faces of the tunnel lining surface can be photographed, which rotates the fixing member in the circumferential direction of the tunnel lining surface, wherein the fixing member is L-shaped and 900 rotatable around the drive axis in the circumferential direction of the tunnel lining surface, the plurality of line sensors are arranged along the circumferential direction of the tunnel lining surface on the L-shaped member, and the drive axis is driven so that the L-shaped member is 900 rotated in the circumferential direction of the tunnel lining surface.

* * * * *